United States Patent
Jawaharlal et al.

(10) Patent No.: US 10,344,326 B2
(45) Date of Patent: Jul. 9, 2019

(54) MAGNETIC FLUX DENSITY BASED DNA SEQUENCING

(71) Applicant: International Business Machines Corporation, Armonk, NY (US)

(72) Inventors: Samuel Mathew Jawaharlal, Chennai (IN); Arunachalam Narayanan, Chennai (IN); Sathya Santhar, Chennai (IN); Balamurugaramanathan Sivaramalingam, Paramakudi (IN)

(73) Assignee: International Business Machines Corporation, Armonk, NY (US)

( * ) Notice: Subject to any disclaimer, the term of this patent is extended or adjusted under 35 U.S.C. 154(b) by 325 days.

(21) Appl. No.: 15/163,735

(22) Filed: May 25, 2016

(65) Prior Publication Data

US 2017/0342478 A1 Nov. 30, 2017

(51) Int. Cl.
| | | |
|---|---|---|
| C12Q 1/68 | (2018.01) | |
| G01R 33/02 | (2006.01) | |
| C12Q 1/6869 | (2018.01) | |
| G01N 27/72 | (2006.01) | |
| G01R 33/04 | (2006.01) | |
| G01R 33/12 | (2006.01) | |

(52) U.S. Cl.
CPC ........... *C12Q 1/6869* (2013.01); *G01N 27/72* (2013.01); *G01R 33/02* (2013.01); *G01R 33/04* (2013.01); *G01R 33/12* (2013.01); *G01R 33/1269* (2013.01)

(58) Field of Classification Search
None
See application file for complete search history.

(56) References Cited

U.S. PATENT DOCUMENTS

| | | |
|---|---|---|
| 5,171,534 A | 12/1992 | Smith et al. |
| 5,374,527 A | 12/1994 | Grossman |
| 5,674,743 A | 10/1997 | Ulmer |
| 7,962,427 B2 | 6/2011 | Tsirigos et al. |
| 2005/0136408 A1 | 6/2005 | Tom-Moy et al. |
| 2006/0246497 A1 | 11/2006 | Huang et al. |
| 2009/0093624 A1 | 4/2009 | Rigoutsos et al. |
| 2013/0171636 A1 | 7/2013 | Bensimon et al. |
| 2014/0274732 A1 | 9/2014 | Hanes et al. |

FOREIGN PATENT DOCUMENTS

WO     9610644     4/1996

OTHER PUBLICATIONS

Abraham et al., "Charge calculations in molecular mechanics 6: the calculation of partial atomic charges in nucleic acid bases and the electrostatic contribution to DNA base pairing", Nucleic Acids Research, vol. 16 No. 6 1988, Robert Robinson Laboratories, University of Liverpool, Liverpool L69 3BX, UK, © IRL Press Limited, Oxford, England, pp. 2639-2657.

(Continued)

*Primary Examiner* — Robert T. Crow
(74) *Attorney, Agent, or Firm* — Monchai Chuaychoo

(57) ABSTRACT

In an approach to magnetic flux density based DNA sequencing, a static magnetic field is provided. A chain of nucleotides is passed through the magnetic field. A change in magnetic flux density of the static magnetic field due to an ionic voltage associated with an individual nucleotide or base pair of the chain of nucleotides is measured. An identity of the nucleotide is determined based on the change in magnetic flux density.

8 Claims, 5 Drawing Sheets

(56) References Cited

OTHER PUBLICATIONS

Bejhed et al., "Turn-on optomagnetic bacterial DNA sequence detection using volume-amplified magnetic nanobeads", Biosensors and Bioelectronics, vol. 66, Apr. 15, 2015, pp. 405-411.
Ferguson Welch et al., "Picoliter DNA Sequencing Chemistry on an Electrowetting-based Digital Microfluidic Platform", HHS Public Access, Published in final edited form as: Biotechnol J. Feb. 2011; 6(2): 10.1002/biot.201000324, 9 pages.
Ferreira et al., "Magnetic field-assisted DNA hybridisation and simultaneous detection using micron-sized spin-valve sensors and magnetic nanoparticles", Sensors and Actuators B Chemical, Jun. 2005, DOI: 10.1016/j.snb.2004.12.071, © 2005 Elsevier B.V., 10 pages.
Linnarsson, Sten, "Magnetic Sequencing", News and Views, © 2012 Nature America, Inc., Nature Methods, vol. 9 No. 4, Apr. 2012, pp. 339-341.
Preub et al., DNA Base Properties from First Principles Plane-Wave Calculations, Computational Materials Science Group, Friedrich-Schiller-Universitat, Max-Wien Platz 1, 07743, Jena, Germany, printed on Mar. 28, 2016, 9 pages.
Rojeab, Adnan Y., "Magnetic Properties Govern the Processes of DNA Replication and the Shortening of the Telomere", World Academy of Science, Engineering and Technology International Journal of Biological, Biomolecular, Agricultural, Food and Biotechnological Engineering vol. 7, No. 7, 2013, 6 pages.
Sawakami-Kobayashi et al., "Multipurpose Robot for Automated Cycle Sequencing", Product Application Focus, BioTechniques 34:634-637 (Mar. 2003), 4 pages.
Svitil, Kathy, "Caltech and IBM Scientists Use Self-Assembled DNA Scaffolding to Build Tiny Circuit Boards", Caltech, Aug. 17, 2009, <http://www.caltech.edu/news/caltech-and-ibm-scientists-use-self-assembled-dna-scaffolding-build-tiny-circuit-boards-1559>, 2 pages.
Vidoudez et al., "Gel Electrophoresis Separating DNA and Proteins", Analytische Chemie I, IAAC, printed on Mar. 25, 2016, 13 pages.
"Atomic Magnetometers", How Atomic Magnetometers Work, Geometrics, <http://mfam.geometrics.com/atomicmagnetomet.html>, 1 page.
"Biot-Savart law", From Wikipedia, the free encyclopedia, <https://en.wikipedia.org/wiki/Biot-Savart_law>, page was last modified on Mar. 4, 2016, 4 pages.
"DNA: nanopore sequencing—Applications—Oxford Nanopore Technologies", <https://www.nanoporetech.com/applications/dna-nanopore-sequencing>, © 2008-2016, 1 page.
"DNA Transistor", IBM, Our people, <http://researcher.watson.ibm.com/researcher/view_group.php?id=1120>, last updated Mar. 19, 2012, 2 pages.
"DNA Transistor", You Tube, IBM Social Media, IBM DNA Transistor, The Future of Genome Sequencing, Uploaded on Oct. 5, 2009, <https://www.youtube.com/watch?v=pKi30ai35mU&index=2&list=PL3A6826FE2D5ED022>, 2 pages.
"Genomic Medicine", IBM, Our people, Updated Jan. 6, 2016, <http://researcher.watson.ibm.com/researcher/view_group.php?id=5347>, 2 pages.
"IBM's Watson to help sequence cancer DNA", USA Today, Mar. 19, 2014, <http://www.usatoday.com/story/tech/2014/03/19/watson-ibm-genome-center-cancer/6604937/>, 1 page.

MAGNETIC FLUX DENSITY BASED DNA SEQUENCING

BACKGROUND

The present disclosure relates generally to the field of genomic (DNA) computing, and more particularly to methods for DNA sequencing.

DNA computing is a rapidly evolving interdisciplinary field combining biochemistry and molecular biology with computational theory to solve problems. DNA computing leverages properties of DNA to determine answers to problems encoded in DNA strands in a massively parallel fashion.

DNA sequencing is an integral part of modern DNA computing techniques. Sequences for thousands of organisms have been decoded and stored in databases, and in turn used in various fields such as machine learning, genomic medicine, and so forth.

Conventional methods and tools for DNA sequencing include, for example but without limitation, primer extension using a DNA polymerase, direct blotting electrophoresis, radioactive defective nucleotides, SDS-PAGE electrophoresis, Maxam-Gilbet sequencing, ion torrent semiconductor sequencing, and tunneling current DNA sequencing.

Current research is mainly focused on nanopore sequencing using tunneling currents, which allows for faster and more accurate results. A nanopore-based device provides single-molecule detection based on electrophoretically driving DNA molecules (i.e., their nucleotides, adenine, cytosine, guanine, and thymine) in solution through a nano-scale pore. Nucleotides are identified based on ionic conductance variation due to the movement of nucleotides in an electrochemical circuit.

SUMMARY

A method for magnetic flux density based DNA sequencing includes providing a static magnetic field. A chain of nucleotides is passed through the magnetic field. A change in magnetic flux density of the static magnetic field due to an ionic voltage associated with an individual nucleotide or base pair of the chain of nucleotides is measured. An identity of the nucleotide is determined based on the change in magnetic flux density.

DETAILED DESCRIPTION

Embodiments described herein enable DNA sequencing based on measuring a change in magnetic flux density as nucleotides are passed through a static magnetic field.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of the invention as set forth hereinafter.

The scope of the present invention is to be determined by the claims. Accordingly, any features, characteristics, advantages, or the like, discussed below in the discussion of embodiments of this specification shall not be taken to mean that such features, characteristics, advantages, or the like are required to practice the present invention as defined by the claims.

Figure 1:
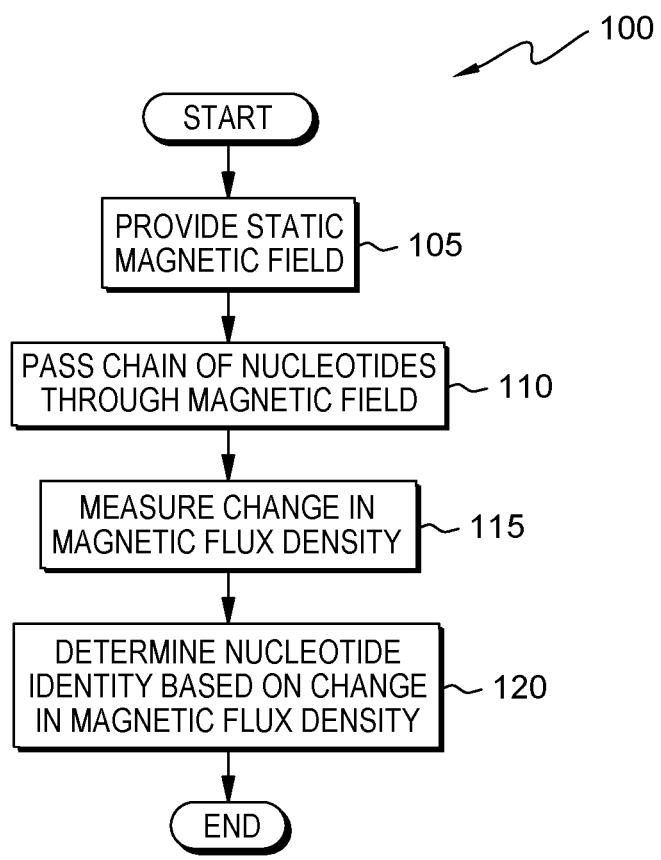
FIG. 1 is a flowchart depicting a method for magnetic flux density based DNA sequencing, in accordance with at least one embodiment of the present invention.

Embodiments of the present invention are described with reference to the Figures. FIG. 1 is a flowchart depicting an embodiment of a method 100 for magnetic flux density based DNA sequencing. As depicted, method 100 includes providing (105) a static magnetic field; passing (110) a chain of nucleotides through the magnetic field; measuring (115) a change in magnetic flux density; and determining (120) an identity of a nucleotide based on the change in magnetic flux density.

Providing (105) a static magnetic field may include using an electromagnet and coil of wire to produce a magnetic field. In another non-limiting embodiment, a static magnetic field may be produced using permanent magnets.

Figure 2A:
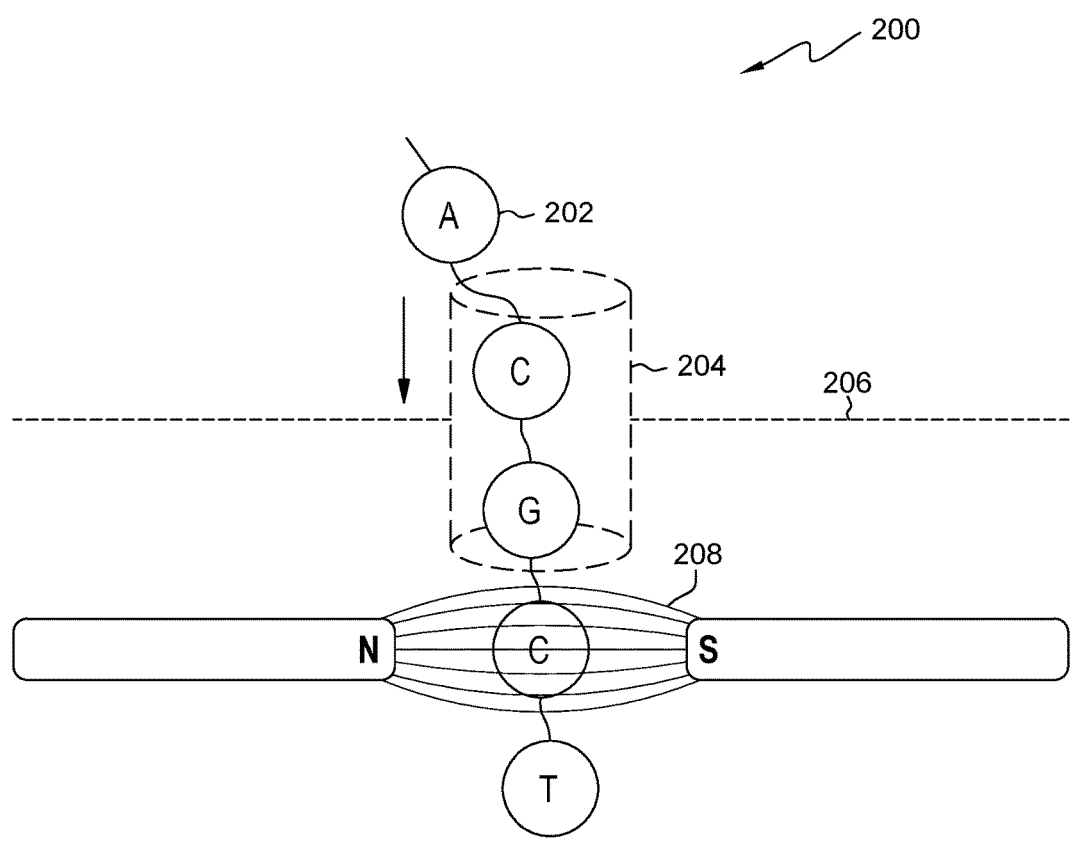
FIG. 2A is a diagram of a passing operation for single-stranded nucleotides, for an embodiment of the method of FIG. 1.
Figure 2B:
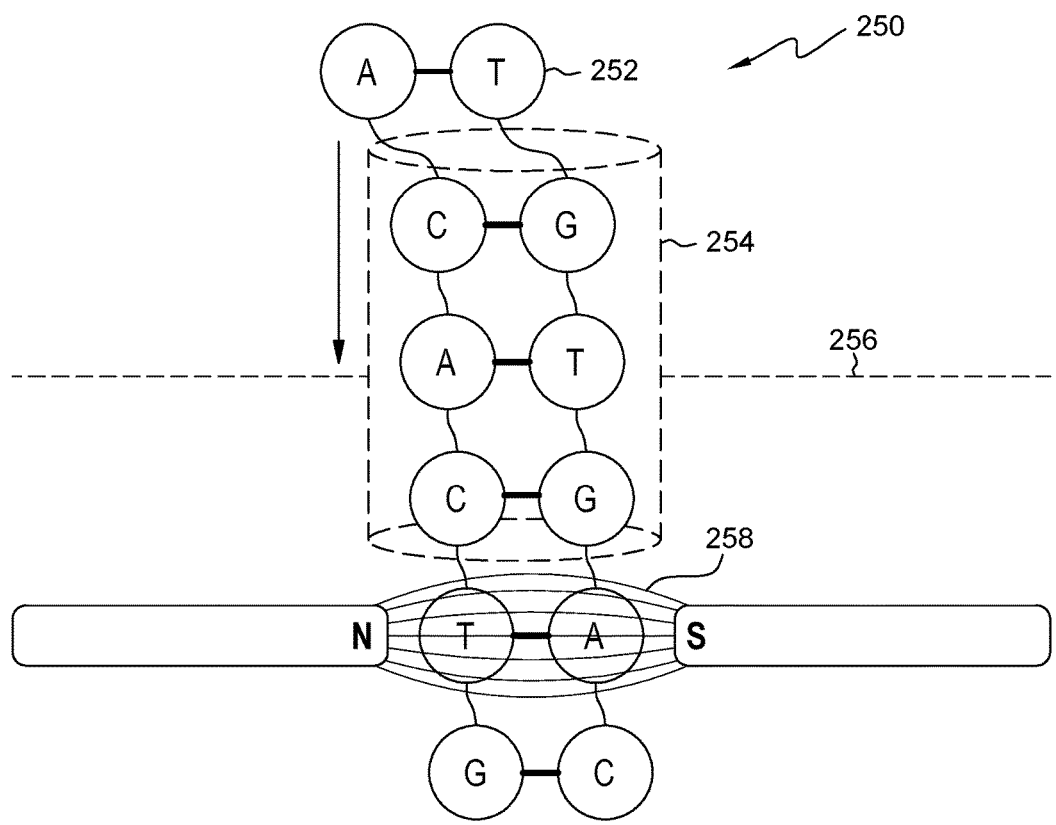
FIG. 2B is a diagram of a passing operation for double-stranded nucleotides, for an embodiment of the method of FIG. 1.

Passing (110) a chain of nucleotides through the magnetic field may include passing single or paired nucleotides through a nanopore. Only one nucleotide, or one pair of nucleotides (or "base pair"), depending on the device setup, should be passed through the magnetic field at a time in order to avoid false results. Movement of the nucleotides occurs because of the charges carried by the nucleotides in the magnetic field. Additional details of passing operation 110 are disclosed herein with reference to FIG. 2A-B.

Measuring (115) a change in magnetic flux density may include using a high-precision magnetometer to measure a change in the magnetic flux density of the magnetic field due to an ionic voltage associated with an individual nucleotide of the chain of nucleotides. For example, the magnetometer can be used to detect magnetic field changes at regular intervals based on the velocity of the nucleotides moving through the nanopore and magnetic field. The type of magnetometer used in measuring operation 115 should be selected based on ability to detect small changes in magnetic field with high accuracy. Measurements may be taken at any point within the magnetic field, e.g., in close proximity to the nanopore.

Figure 3:
FIG. 3 is table of ionization potential values for individual nucleotides and base pairs, respectively, used in a determining operation, for an embodiment of the method of FIG. 1.
Figure 4:
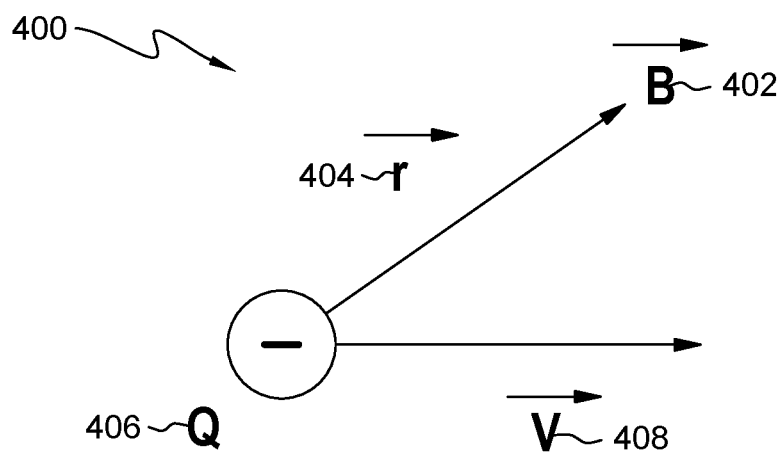
FIG. 4 is a diagram of the relationship between magnetic field, displacement, charge, and velocity used in a determining operation, for an embodiment of the method of FIG. 1.

Determining (120) an identity of a nucleotide based on the change in magnetic flux density may include applying the Biot-Savart law to the change, where the Biot-Savart law describes a magnetic field generated by an electric current in terms of magnitude, direction, length, and proximity of the current. Additional details of determining operation 120 are disclosed herein with reference to FIGS. 3 and 4.

As shown in diagram 200 (FIG. 2A), a single chain 202 of nucleotides may be passed through a nanopore 204 in plate 206, in a static magnetic field 208.

As shown in diagram 250 (FIG. 2B), the device setup can be altered to accommodate passage of a double strand 252 of nucleotides through nanopore 254 in plate 256, in static magnetic field 258. Magnetic field 258 can be adjusted to ensure that only one base pair passes through the field at a time.

As shown in table 300 (FIG. 3), individual nucleotides and pairs of nucleotides are associated with respective and identifying ionization potentials. The differences in ionization potential are based on the fact that each nucleotide (i.e., adenine, cytosine, guanine, thymine) or combination of nucleotides differs in features such as number of C, H, O, and N atoms; number of hydrogen bonds; number of free electrons; polarity; and bond length.

As shown in diagram 400 (FIG. 4), a relationship between magnetic field 402, displacement 404, point charge 406, and velocity 408 can be leveraged for nucleotide identification in determining operation 120. Displacement 404 of point charge 406 at velocity 408 through magnetic field 402 causes a deflection of magnetic field 402.

The Biot-Savart law can be applied to the deflection illustrated by diagram 400 in order to identify an individual nucleotide or pair of nucleotides. For example, the Biot-Savart law for a point charge can be applied to a point charge 406 moving at a constant velocity 408 according to the following relationships, wherein $\mu_o$ is the permeability constant, q is the magnitude of point charge 406, and boldface type is used to represent a vector quantity:

$$B = \frac{\mu_0}{4\pi} \frac{qvr}{r^3}$$

$$|B| = \frac{\mu_0}{4\pi} \frac{qv\sin\theta}{r^2}$$

Velocity 408 of the chain of nucleotides in a gel medium is affected by voltage, concentration of the gel, composition of the gel, and size of the chain. A constant velocity 408 can be achieved if these factors are kept constant throughout passing operation 110 and measuring operation 115.

Respective theoretical changes in magnetic flux density may be associated with each nucleotide and base pair based on the above parameters (e.g., velocity 408, θ, r). Actual changes observed in measuring operation 115 can be plotted in order to identify nucleotides and base pairs that produced a deflection matching a theoretical value.

In addition to the steps and operations disclosed herein, additional steps and operations may be performed while retaining the spirit and intent of the disclosed embodiments. Operations of method 100 may produce data that is used in turn for machine learning, predictive analytics, and other DNA computing applications. In one of many possible examples, the information in DNA as revealed through DNA sequencing methods can be used in research seeking personalized cancer treatments.

Figure 5:
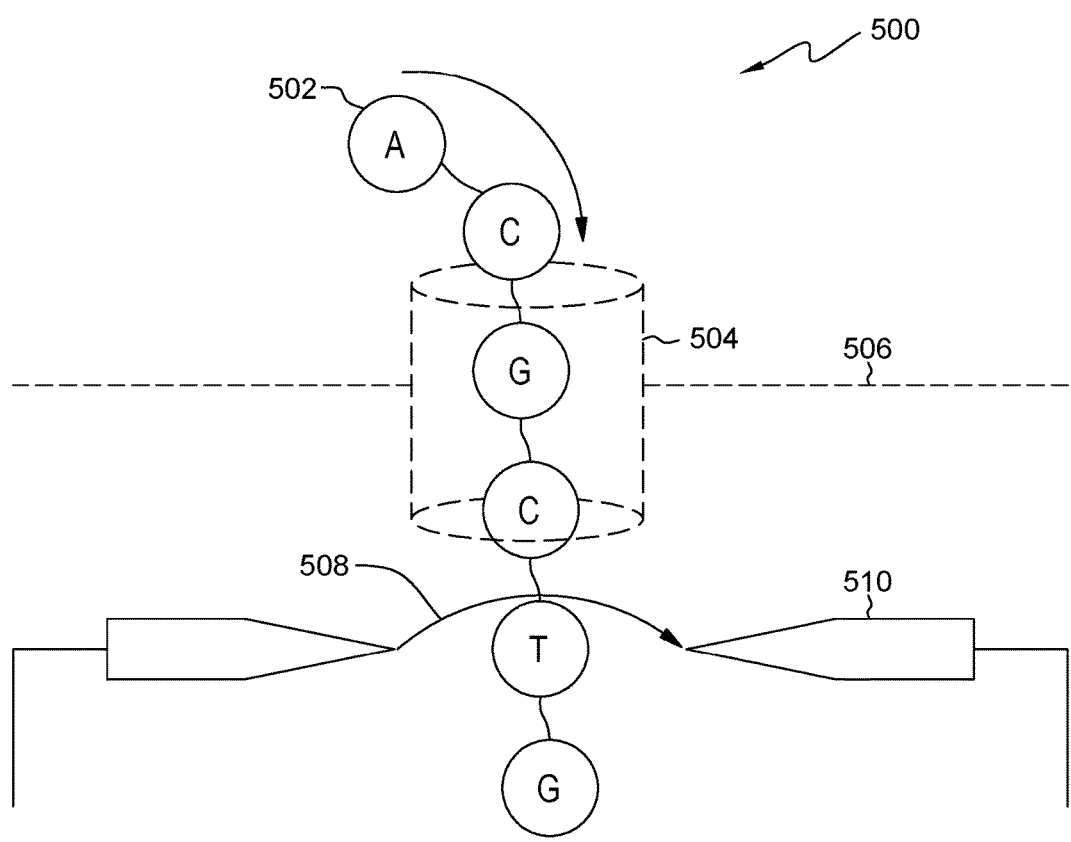
FIG. 5 is a diagram of a passing operation for single-stranded nucleotides, in accordance with conventional technology.

Diagram 500 (FIG. 5) illustrates an example of DNA sequencing based on conventional methods. Diagram 500 shows a single strand 502 of nucleotides passed through nanopore 504 in plate 506 and a tunneling current 508 between electrodes 510.

Embodiments of the present invention may recognize one or more of the following facts, potential problems and/or potential areas for improvement with respect to conventional methods for nanopore sequencing using tunneling currents: (i) the gap between the electrodes should be small, in the order of nanometers, to allow only a single chain of nucleotides to pass through, so 2-3 nucleotides of DNA may contribute to the ionic current blockade, resulting in greater than expected resistance and, in turn, false results; (ii) experimental device setup must be altered to allow a chain of complementary base pairs (as opposed to unpaired nucleotides) to pass through, increasing the cost of the infrastructure; and/or (iii) the flow of tunneling current through a single nucleotide alters the bonding structure of the nucleotide, affecting stability.

Embodiments of the present invention may include one or more of the following features, characteristics, and/or advantages: (i) the device setup can be used for identifying sequences for both single and double-stranded DNA without additional infrastructure, making the setup inexpensive in comparison with conventional methods; (ii) device set-up is simple in comparison with conventional methods, requiring only a single electromagnet and coil of wire to provide a magnetic field; (iii) high-precision magnetometers can be used to measure change in magnetic flux density quickly and with low noise increasing usefulness for advanced analytics and machine learning applications; (iv) high-precision magnetometers can be used to measure magnetic changes even at the atomic level; and/or (v) because there is no flow of electric current (as in the case of tunneling based sequencing), long sequence readouts are possible without change in the structure of the DNA pairs or kinetics of the ecosystem.

It should be noted that this description is not intended to limit the invention. On the contrary, the embodiments presented are intended to cover some of the alternatives, modifications, and equivalents, which are included in the spirit and scope of the invention as defined by the appended claims. Further, in the detailed description of the disclosed embodiments, numerous specific details are set forth in order to provide a comprehensive understanding of the claimed invention. However, one skilled in the art would understand that various embodiments may be practiced without such specific details.

Although the features and elements of the embodiments disclosed herein are described in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for magnetic flux density based DNA sequencing, the method comprising:
    providing a static magnetic field;
    passing a chain of nucleotides through the static magnetic field;
    measuring a change in magnetic flux density of the static magnetic field due to an ionic voltage associated with an individual nucleotide or base pair of the chain of nucleotides; and
    determining an identity of the individual nucleotide or the base pair of the chain of nucleotides based on the change in magnetic flux density.

2. The method of claim 1, wherein providing a static magnetic field further comprises:
    generating a static magnetic field using permanent magnets or a single electromagnet associated with a coil of wire.

3. The method of claim 1, wherein passing a chain of nucleotides through the static magnetic field further comprises:
    passing the chain of nucleotides through a nanopore device and a gel medium.

4. The method of claim 1, wherein the chain of nucleotides comprises a single strand of nucleotides.

5. The method of claim 1, wherein the chain of nucleotides comprises double-stranded nucleotides.

6. The method of claim 1, wherein measuring a change in magnetic flux density of the static magnetic field further comprises:
    measuring magnetic field changes using a high precision magnetometer.

7. The method of claim 6, wherein the magnetometer detects magnetic field changes at predefined intervals based on a velocity of the chain of nucleotides.

8. The method of claim 1, wherein determining an identity of the nucleotide further comprises:
    applying the Biot-Savart law for a point charge to a deflection of the static magnetic field.

* * * * *